(12) United States Patent
Sethuraman et al.

(10) Patent No.: US 11,298,028 B2
(45) Date of Patent: Apr. 12, 2022

(54) TEMPERATURE DISTRIBUTION DETERMINATION APPARATUS

(71) Applicant: KONINKLIJKE PHILIPS N.V., Eindhoven (NL)

(72) Inventors: Shriram Sethuraman, Woburn, MA (US); Ajay Anand, Fishkill, NY (US); Sheng-Wen Huang, Ossining, NY (US); Francois Guy Gerard Marie Vignon, Croton on Hudson, NY (US); Ameet Kumar Jain, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1035 days.

(21) Appl. No.: 15/116,278

(22) PCT Filed: Feb. 2, 2015

(86) PCT No.: PCT/EP2015/052082
§ 371 (c)(1),
(2) Date: Aug. 3, 2016

(87) PCT Pub. No.: WO2015/121096
PCT Pub. Date: Aug. 20, 2015

(65) Prior Publication Data
US 2016/0345839 A1    Dec. 1, 2016

Related U.S. Application Data

(60) Provisional application No. 61/938,716, filed on Feb. 12, 2014.

(30) Foreign Application Priority Data

Mar. 18, 2014    (EP) .................................. 14160505

(51) Int. Cl.
*A61B 5/01* (2006.01)
*A61B 8/08* (2006.01)
(Continued)

(52) U.S. Cl.
CPC ............ *A61B 5/015* (2013.01); *A61B 5/0036* (2018.08); *A61B 8/0841* (2013.01); *A61B 8/48* (2013.01);
(Continued)

(58) Field of Classification Search
CPC .......... A61B 2018/00529; A61B 2018/00577; A61B 2018/00791; A61B 5/015;
(Continued)

(56) References Cited

U.S. PATENT DOCUMENTS 4,994,965 A * 2/1991 Crawford .............. G06T 11/005
378/95
5,657,760 A    8/1997 Ying et al.
(Continued)

FOREIGN PATENT DOCUMENTS

EP    2387963 A1    11/2011
JP    562217946 A    9/1987
(Continued)

OTHER PUBLICATIONS

Lemor, R., "Nicht-invasive Kontrolle thermischer Therapien mit Hilfe des Ultraschalls: Untersuchungen am Beispiel der Laser-Therapie", Humboldt University of Berlin (2001), Abstract.
(Continued)

*Primary Examiner* — Carolyn A Pehlke
(74) *Attorney, Agent, or Firm* — Sherry Austin (57) ABSTRACT

The invention relates to a temperature distribution determination apparatus for determining a temperature distribution within an object (20), while an energy application element (2) applies energy to the object, especially while an ablation (Continued)

procedure for ablating a tumor within an organ is performed. A time-dependent first ultrasound signal is generated for an ultrasound measurement region within the object and a temperature distribution within the object is determined based on the generated time-dependent first ultrasound signal and based on a position of the energy application element (2) relative to the ultrasound measurement region tracked over time. This can ensure that always the correct position of the energy application element, which may be regarded as being a heat source, is considered, even if the energy application element moves, for instance, due to a movement of the object. This can lead to a more accurate determination of the temperature distribution.

17 Claims, 3 Drawing Sheets (51) Int. Cl.
    *G01K 11/24*     (2006.01)
    *A61B 18/00*     (2006.01)
    *A61B 18/14*     (2006.01)
    *A61B 5/00*     (2006.01)
    *G01K 13/20*     (2021.01)
    *A61B 34/20*     (2016.01)
    *A61B 90/00*     (2016.01)
    *A61B 34/10*     (2016.01)

(52) U.S. Cl.
    CPC ........ *A61B 8/5276* (2013.01); *A61B 18/1477* (2013.01); *G01K 11/24* (2013.01); *G01K 13/20* (2021.01); *A61B 2018/00529* (2013.01); *A61B 2018/00577* (2013.01); *A61B 2018/00791* (2013.01); *A61B 2034/101* (2016.02); *A61B 2034/2063* (2016.02); *A61B 2090/3929* (2016.02); *G01K 2213/00* (2013.01)

(58) Field of Classification Search
    CPC ....... A61B 5/4836; A61B 8/0841; A61B 8/48; A61B 8/5276; A61B 18/1477; A61B 2034/101; A61B 2034/2063; A61B 2090/3929; G01K 11/24; G01K 13/002; G01K 2213/00
    See application file for complete search history.

(56) References Cited

U.S. PATENT DOCUMENTS

| | | | |
|---|---|---|---|
| 6,576,875 | B1 | 6/2003 | Kleffner et al. |
| 9,999,789 | B2 | 6/2018 | Kuhn |
| 2001/0007940 | A1 | 7/2001 | Tu et al. |
| 2004/0030227 | A1 | 2/2004 | Littrup et al. |
| 2009/0171188 | A1* | 7/2009 | Paul et al. |
| 2009/0312637 | A1 | 12/2009 | Balasundara et al. |
| 2011/0060221 | A1 | 3/2011 | Fan et al. |
| 2011/0201973 | A1 | 8/2011 | Stephens |
| 2011/0288410 | A1 | 11/2011 | Speyer et al. |
| 2012/0010479 | A1 | 1/2012 | Eusemann et al. |
| 2012/0165666 | A1 | 6/2012 | Megens et al. |
| 2012/0172708 | A1 | 7/2012 | Anand et al. |
| 2012/0277763 | A1 | 11/2012 | Greenblatt et al. |
| 2013/0041252 | A1 | 2/2013 | Vignon et al. |
| 2013/0060243 | A1 | 3/2013 | Kuhn |
| 2013/0223702 | A1* | 8/2013 | Holsing ................. A61B 5/061 382/128 |
| 2013/0303880 | A1* | 11/2013 | Hsu ........................ A61B 5/015 600/411 |
| 2019/0015072 | A1 | 1/2019 | Szabolcs et al. |

FOREIGN PATENT DOCUMENTS

| | | | |
|---|---|---|---|
| WO | 2008112005 | A1 | 9/2008 |
| WO | 2011046880 | A3 | 8/2011 |
| WO | WO-2011145020 | A1 * | 11/2011 ............. A61B 18/00 |

OTHER PUBLICATIONS

Anand, A., et al., "Three-dimensional spatial and temporal temperature imagining in gel phantoms using backscattered ultrasound", IEEE Transactions on Ultrasonics, Ferroelectrics and Frequency Control, 54(1), pp. 23-31 (2007).

Mung, J. et al., "A Non-disruptive Technology for Robust 3D Tool Tracking for Ultrasound-Guided Interventions", MICCAI 1, vol. 6891 of Lecture Notes in Computer Science, pp. 153-160, (2011).

Pennes, H.H., "Analysis of tissue and arterial blood temperatures in the resting human forearm", 85:5-34, Journal of Applied Physiology (1998).

Maruyama, S., et al., "Estimation of temperature distribution in biological tissue by using solutions of bioheat transfer equation", Heat Transfer Asian Research, vol. 37, No. 6, 2008, pp. 374-386.

Simon, C., et al., "Motion compensation algorithm for non-invasive two-dimensional temperature estimation using diagnostic pulse-echo ultrasound", Proceedings of SPIE, SPIE—International Society for Optical Engineering, vol. 3249, 1998, pp. 182-192.

Arthur, R.M., et al., "Non-invasive estimation of hyperthermia temperatures with ultrasound", International Journal of Hyperthermia, vol. 21, No. 6, 2005, pp. 589-600.

\* cited by examiner

TEMPERATURE DISTRIBUTION DETERMINATION APPARATUS

CROSS-REFERENCE TO PRIOR APPLICATIONS

This application is the U.S. National Phase application under 35 U.S.C. § 371 of International Application Serial No. PCT/EP2015/052082, filed on Feb. 2, 2015, which claims the benefit of U.S. Application Ser. No. 61/938,716, filed on Feb. 12, 2014 and European Patent Application No. 14160505.5, filed on Mar. 18, 2014. These applications are hereby incorporated by reference herein.

FIELD OF THE INVENTION

The invention relates to a temperature distribution determination apparatus, method and computer program for determining a temperature distribution within an object. The invention relates further to an energy application system for applying energy to the object.

BACKGROUND OF THE INVENTION

The thesis "Nicht-invasive Kontrolle thermischer Therapien mit Hilfe des Ultraschalls: Untersuchungen am Beispiel der Laser-Therapie" by R. Lemor, Humboldt University of Berlin (2001) discloses a temperature distribution determination apparatus for determining a temperature distribution within an object to which heat is applied by using a laser applicator. The temperature distribution determination apparatus is adapted to generate several ultrasound images of the object at different times, to determine the positions of the laser applicator in the several ultrasound images and to use these positions for registering the ultrasound images to each other. The temperature is then determined by ultrasound thermometry based on the registered images.

U.S. Pat. No. 6,576,875 B1 discloses a device for controlling a selective application of heat into a material. The device comprises an ultrasound wave generation unit adapted to couple ultrasound waves to the material, an ultrasound wave detection unit adapted to detect ultrasound waves emerging from the material and an evaluation unit adapted to generate parameters providing information about thermal and structural changes inside the material based on the detected ultrasound waves. The device further comprises a heat application unit for directing heat to the material. The ultrasound wave generation unit and the ultrasound wave detection unit are positioned to permit coupling of the ultrasound waves to and detecting of the ultrasound waves from a same location within the material and they are adjustable relative to the material and the heat application unit. The heat application unit is disposed in a center of the ultrasound wave generation unit and the ultrasound wave detection unit.

In ultrasound thermometry ultrasound waves are sent into an object, ultrasound waves, which are backscattered within the object, are detected and a temperature distribution within the object is determined based on the detected backscattered ultrasound waves. The determination of the temperature distribution depending on the backscattered ultrasound waves is based on the fact that the speed of sound within the object changes as a function of temperature which manifests as apparent shifts, i.e. displacements, in the backscattered ultrasound waves. Although in case of static objects ultrasound thermometry allows for an accurate determination of the temperature distribution, in moving objects the accuracy of the temperature distribution determined by ultrasound thermometry can be reduced.

SUMMARY OF THE INVENTION

The invention relates to a temperature distribution determination apparatus, method and computer program for determining a temperature distribution within an object, which allow for an accurate determination of the temperature distribution, even if the object moves. It is a further object of the present invention to provide an energy application system for applying energy to an object, which comprises the temperature distribution determination apparatus.

In a first aspect of the present invention a temperature distribution determination apparatus for determining a temperature distribution within an object, while an energy application element applies energy to the object, is presented, wherein the temperature distribution determination apparatus comprises:

an ultrasound device for sending ultrasound waves into an ultrasound measurement region within the object, receiving ultrasound waves from the ultrasound measurement region and generating a time-dependent first ultrasound signal based on the received ultrasound waves, a tracking device for tracking the position of the energy application element within the object relative to the ultrasound measurement region over time, wherein the tracking device comprises a) an ultrasound sensor attached to the energy application element and adapted to receive the ultrasound waves from the ultrasound device and to generate a second ultrasound signal based on the received ultrasound waves and b) a position determination unit for determining the position of the energy application element based on the received second ultrasound signal, a temperature distribution determination unit for determining a temperature distribution within the object based on the generated time-dependent first ultrasound signal and based on the position of the energy application element tracked over time.

Since the temperature distribution determination unit also considers the position of the energy application element while determining the temperature distribution, it can be ensured that always the correct position of the energy application element, which applies energy to the object and which may be regarded as being a heat source, relative to the ultrasound measurement region is considered, even if the energy application element moves, for instance, due to a movement of the object. This can lead to a more accurate determination of the temperature distribution.

The ultrasound measurement region may be a plane, which may also be regarded as being a scan plane that is ultrasonically scanned. The ultrasound measurement region may comprise one or several planes, which may be parallel or orthogonal to each other. The ultrasound device can comprise a two-dimensional or three-dimensional ultrasound probe, i.e. an ultrasound probe comprising a one-dimensional or two-dimensional array of ultrasound transducers for ultrasonically scanning a two-dimensional or three-dimensional, respectively, ultrasound measurement region. The ultrasound device may also be used to image the object, in order to find insertion paths within the object, along which the energy application element could be inserted into the object before applying the energy.

The object is preferably a part of a living being like a person or an animal. In particular, the object may be the liver or another organ, wherein the energy application element can be adapted to ablate a tumor region or another region within the liver or the other organ.

In an embodiment the temperature distribution determination unit is adapted to, in a lower temperature range, a) determine a time-dependent first temperature distribution in the ultrasound measurement region based on the generated time-dependent first ultrasound signal, b) provide a model describing a time-dependent model temperature distribution within the object depending on modifiable model parameters and depending on the position of the energy application element tracked over time, and c) determine model parameters based on the tracked position of the energy application element and based on the provided model by modifying the model parameters such that the model temperature distribution is adapted to the first temperature distribution in the ultrasound measurement region, in particular, such that a deviation of the model temperature distribution from the first temperature distribution in the ultrasound measurement region is minimized, wherein the temperature distribution determination unit is further adapted to, in a higher temperature range, d) determine a second temperature distribution within the object based on the provided model and the determined model parameters. The lower temperature range is preferentially a temperature range in which temperatures are measurable by ultrasound thermometry, whereas the higher temperature range is preferentially a temperature range in which temperatures are not measurable by ultrasound thermometry. The model may depend on further parameters like the amount of heat applied by the energy application element and the times at which the heat is applied, wherein in this case, while determining the model parameters and while determining the second temperature distribution, also these further parameters may be considered. The model parameters are, for instance, thermal and electrical conductivities of the object.

The temperature distribution determination unit may be adapted to determine the time-dependent first temperature distribution based on the generated time-dependent first ultrasound signal and based on the position of the energy application element tracked over time. In particular, the object may be a periodically moving object, which may move due to respiration, and the energy application element may be in contact with the object, in order to apply the energy to the object, and move with the object, wherein the temperature distribution determination unit may be adapted to a) determine a motion phase of the motion of the object based on the position of the energy application element tracked over time, and b) use for the determination of the first temperature distribution over time the first ultrasound signal at times that correspond to the determined motion phase. For instance, a motion profile or motion waveform may be determined from the position of the energy application element tracked over time and a certain motion phase may be determined from the motion profile or motion waveform. It is preferred that the determined motion phase is a quiescent phase of the motion. The temperature distribution determination unit can therefore be adapted to provide a motion-gated first temperature distribution.

If for determining the time-dependent first temperature distribution the first ultrasound signal is used at times only that correspond to the same motion phase in different motion periods, it is likely that the parts of the ultrasound signal, for instance, respective two-dimensional or three-dimensional ultrasound frames, relate to the same part of the object. This can lead to an improved accuracy of the determined time-dependent first temperature distribution and thus to an improved determination of the model parameters, which is based on the time-dependent first temperature distribution, and an improved accuracy of the second temperature distribution which in turn is determined based on the determined model parameters.

The temperature distribution determination unit preferentially uses known ultrasound thermometry techniques for determining the first temperature distribution based on the first ultrasound signal. For instance, the first temperature distribution determination unit may be adapted to use the technique described in the article "Three-dimensional spatial and temporal temperature imaging in gel phantoms using backscattered ultrasound" by A. Anand et al., IEEE Transactions on Ultrasonics, Ferroelectrics and Frequency Control, 54(1), pages 23 to 31 (2007), which is herewith incorporated by reference, which in pertinent part provides:

II. ULTRASONIC TEMPERATURE ESTIMATION TECHNIQUE

A. Theory

When a region of tissue is heated, the resulting temperature rise results in variations in the speed of sound and tissue thermal expansion [17]. As a result, the backscattered ultrasound echoes from the heated region undergo time shifts, and these time shifts can be mapped into apparent spatial displacements assuming a nominal sound speed (typically 1540 m/s). Theoretically, accompanying these apparent spatial displacements are real displacements of ultrasonic scattering volumes due to thermal expansion. However, for temperature rises in the range of 10-15° C. above body temperature in biological tissues, the effect of thermal expansion can be ignored [12], [18].

It was shown previously that the measured apparent displacements are related to the temperature change by the following equation [13], [15]:

$$a_c \Delta T = -du(y)/dy, \quad (1)$$

where $\Delta T$ represents the temperature change, $u(y)$ represents the profile of the apparent displacement measured along the direction of propagation of the ultrasound beam (y) and $a_c$ represents the coefficient of thermal dependence of sound speed in units of °$C.^{-1}$. The dimensionless quantity $du(y)/dy$ is referred to as temperature-induced strain as it is the spatial gradient of an apparent displacement. Through use of the temperature-induced strain $du(y)/dy$ measured from the ultrasound RF backscatter data acquired during the heating procedure, and by independent knowledge of $a_c$ an acoustical property of tissue, the absolute temperature rise is determined.

B. RE Data Analysis

The apparent displacements, $u(y)$, are estimated by tracking the ultrasound echo shifts between ultrasound scan lines at the same spatial location on a pair of RF data frames (one acquired before heating commenced and the other acquired during heating and subsequent cool down) using a time-domain based, 1-D normalized cross-correlation technique similar to that used in the field of elastography [19]. The RF scan lines are divided into a series of segments of length 3 mm with 60% overlap. For each segment, a 1-D cross-correlation search is used to find the best match for this segment within a search region defined around the same spatial location on the RF line acquired later in time. Time shifts smaller than one RF sampling period are estimated by locating the maximum of a parabola that is fit around the peak of the cross-correlation function [20], using three adjacent RF samples. The time shift within the search region for which the best match is obtained is referred to as the estimated travel time change for the segment. This procedure is repeated for all the segments in a frame to obtain a 3-D travel-time change map corresponding to two successive time increments. By repeating this procedure for consecutive pairs of frames, 3-D temporal maps of the travel-time changes are computed for the whole experiment. These travel-time change maps are scaled by 1540/2 m/s to obtain apparent displacements u(y). The apparent displacements are differentiated along y using a least squares estimator [21] with a kernel length of 7 samples (7.2 mm), and they are scaled using $a_c$ in agreement with (1) to obtain 3-D maps of the local temperature rise. In this study, a sector-shaped ultrasound probe was used for the 3-D RF data collection. A 3-D linear interpolation technique was used to map the strain estimates derived in the spherical coordinate system to the Cartesian coordinate system. The ultrasound thermometry technique is based on the analysis of ultrasound backscatter, i.e. of the first ultrasound signal, at different instants of time. If these different instants of time correspond to the same motion phase, especially to a quiescent phase, the accuracy of determining the first temperature distribution can be increased.

It is also preferred that, if the object is a periodically moving object and the energy application element is in contact with the object, in order to apply the energy to the object, and moves with the object, the temperature distribution determination unit is adapted to use for the determination of the time-dependent first temperature distribution the time-dependent first ultrasound signal at times at which the tracking device determined the same position for the energy application element. This can increase the likelihood that for determining the first temperature distribution only the temporal parts of the first ultrasound signal are used, which correspond to the same part of the object. This can further improve the accuracy of determining the first temperature distribution and thus of the model parameters and of the second temperature distribution that is determined based on the determined model parameters.

The tracking device comprises a) an ultrasound sensor attached to the energy application element and adapted to receive the ultrasound waves from the ultrasound device and to generate a second ultrasound signal based on the received ultrasound waves, and b) a position determination unit for determining the position of the energy application element based on the received second ultrasound signal. Since the ultrasound waves generated by the ultrasound device are used for determining the position of the energy application element and since the propagation region of the ultrasound waves defines the location of the ultrasound measurement region, this kind of determining the position of the energy application element automatically leads to this position relative to the location of the ultrasound measurement region. Thus, the position of the energy application element relative to the location of the ultrasound measurement region can be determined in a relatively simple way, especially without necessarily requiring further localization sensors like electromagnetic (EM) or optical shape sensing (OSS) localization sensors. However, in addition, the tracking device may also be adapted to use EM tracking or OSS tracking for tracking the position of the energy application element relative to the position of the ultrasound measurement region. In particular, EM and/or OSS sensors may be attached to or integrated with the energy application element and the ultrasound device, in order to determine the position of the energy application element relative to the position of the ultrasound measurement region.

The ultrasound sensor can comprise copolymer piezoelectric material for generating the second ultrasound signal based on the received ultrasound waves. The ultrasound sensor is preferentially in a passive mode only, i.e. preferentially it just receives ultrasound waves and generates an ultrasound signal based on the received ultrasound waves. One or several ultrasound sensors can be attached to the energy application element.

The energy application element can comprise an ablation electrode, especially a radio frequency (RF) ablation electrode, for applying ablation energy to the object. The ablation element can comprise a catheter or a needle with the ablation electrode, wherein the ultrasound sensor may be attached to the catheter or needle. The energy application element can also comprise an introducer sheath for introducing the ablation electrode into the object, wherein the ultrasound sensor may be attached to the introducer sheath.

In an embodiment the temperature distribution determination unit is adapted to determine a movement of the object based on the generated time-dependent first ultrasound signal and to determine the temperature distribution based on the generated time-dependent first ultrasound signal, the position of the energy application element tracked over time and the determined movement of the object. For instance, the time-dependent first ultrasound signal can be a time-dependent ultrasound image comprising several two-dimensional or three-dimensional ultrasound frames. Temporally adjacent ultrasound frames may be compared by applying a similarity measure like a cross-correlation procedure, wherein a quiescent motion phase can be determined by determining temporal regions where adjacent ultrasound frames are most similar, i.e., for instance, temporal regions can be determined at which the similarity of temporally adjacent images has a local maximum. The temperature distribution determination unit may then be adapted to use only ultrasound frames, which correspond to the quiescent motion phase, together with the tracked position of the energy application element for determining the temperature distribution. Also this can lead to a further improved accuracy of the determined temperature distribution. For instance, a first time-dependent temperature distribution can be determined based on ultrasound frames only, which correspond to the quiescent phase, by ultrasound thermometry. This first time-dependent temperature distribution may already be the temperature distribution to be finally determined, or it may be further used to determine model parameters of the thermal model described above, wherein the determined model parameters may be used for determining a second temperature distribution within a temperature range in which a temperature distribution is not determinable by ultrasound thermometry.

In an embodiment the object is a periodically moving object and the energy application element is in contact with the object, in order to apply the energy to the object, and moves with the object, wherein the temperature distribution determination unit is adapted to a) determine a motion phase of the motion of the object based on the position of the energy application element tracked over time, and b) use for the determination of the temperature distribution the time-dependent first ultrasound signal at times that correspond to the determined motion phase. Alternatively or in addition, the temperature distribution determination unit may be adapted to use for the determination of the temperature distribution the time-dependent first ultrasound signal at times at which the tracking device determined the same position for the energy application element. The determined temperature distribution may be a first temperature distribution determined by ultrasound thermometry, wherein this first temperature distribution may be shown to a user. The first temperature distribution determined by ultrasound thermometry may be further used to determine model parameters of a thermal model, wherein the determined model parameters can be used together with the thermal model to determine a second temperature distribution in a temperature range, in which the temperature cannot be determined by ultrasound thermometry.

The temperature distribution determination apparatus preferentially further comprises an inner structure providing unit for providing inner structure data being indicative of an inner structure of the object, which influences the temperature distribution, wherein the temperature distribution determination unit may be adapted to determine the temperature distribution based on the generated time-dependent first ultrasound signal, the position of the energy application element tracked over time and the provided inner structure data. If the object is a part of a living being and the energy is applied to the living being for ablating a part of the living being, the temperature distribution determination apparatus preferentially further comprises an ablated region determination unit for determining an ablated region defining a region within the object that has been ablated, wherein the ablated region determination unit is adapted to determine the ablated region by determining a part of the object for which the determined temperature distribution comprises a temperature being larger than a predefined temperature threshold. The region of interest is preferentially a tumor region, which should be ablated completely. The determined ablated region and the tumor region may be displayed, in order to allow a physician to easily compare them and to ensure that the ablated region completely covers the tumor region.

In an embodiment the ultrasound measurement region, especially the ultrasound device and thereby the ultrasound measurement region, is movable with respect to the object, wherein the tracking device is adapted to track the position of the ultrasound measurement region, especially by tracking the position of the ultrasound device, while the ultrasound measurement region is moved relative to the object, wherein the temperature distribution determination unit is adapted to determine the temperature distribution within the object based on the tracked position of the ultrasound measurement region, the generated first ultrasound signal and the tracked position of the energy application element. For instance, for different positions of the ultrasound measurement region temperature distributions can be determined, wherein these temperature distributions can be stitched together to provide a temperature distribution covering a larger part of the object, in particular, the entire object.

In another aspect of the present invention an energy application system for applying energy to an object is presented, wherein the energy application system comprises:

an energy application element for applying the energy to the object, and a temperature distribution determination apparatus for determining a temperature distribution within the object caused by applying the energy to the object as defined in claim 1.

In a further aspect of the present invention a temperature distribution determination method for determining a temperature distribution within an object, while an energy application element applies energy to the object, is presented, wherein the temperature distribution determination method comprises:

sending ultrasound waves into an ultrasound measurement region within the object, receiving ultrasound waves from the ultrasound measurement region and generating a time-dependent first ultrasound signal based on the received ultrasound waves by an ultrasound device, tracking the position of the energy application element within the object relative to the ultrasound measurement region over time by a tracking device, wherein the tracking device comprises an ultrasound sensor, which is attached to the energy application element, which receives the ultrasound waves from the ultrasound device and which generates a second ultrasound signal based on the received ultrasound waves, and a position determination unit which determines the position of the energy application element based on the received second ultrasound signal, and determining a temperature distribution within the object based on the generated time-dependent first ultrasound signal over time and based on the position of the energy application element tracked over time by a temperature distribution determination unit.

In another aspect of the present invention a computer program for determining a temperature distribution within an object is presented, the computer program comprising program code means for causing a temperature distribution determination apparatus as defined in claim 1 to carry out the steps of the temperature distribution determination method as defined in claim 13, when the computer program is run on a computer controlling the temperature distribution determination apparatus.

It shall be understood that the temperature distribution determination apparatus of claim 1, the energy application system of claim 12, the temperature distribution determination method of claim 13, and the computer program for determining a temperature distribution of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
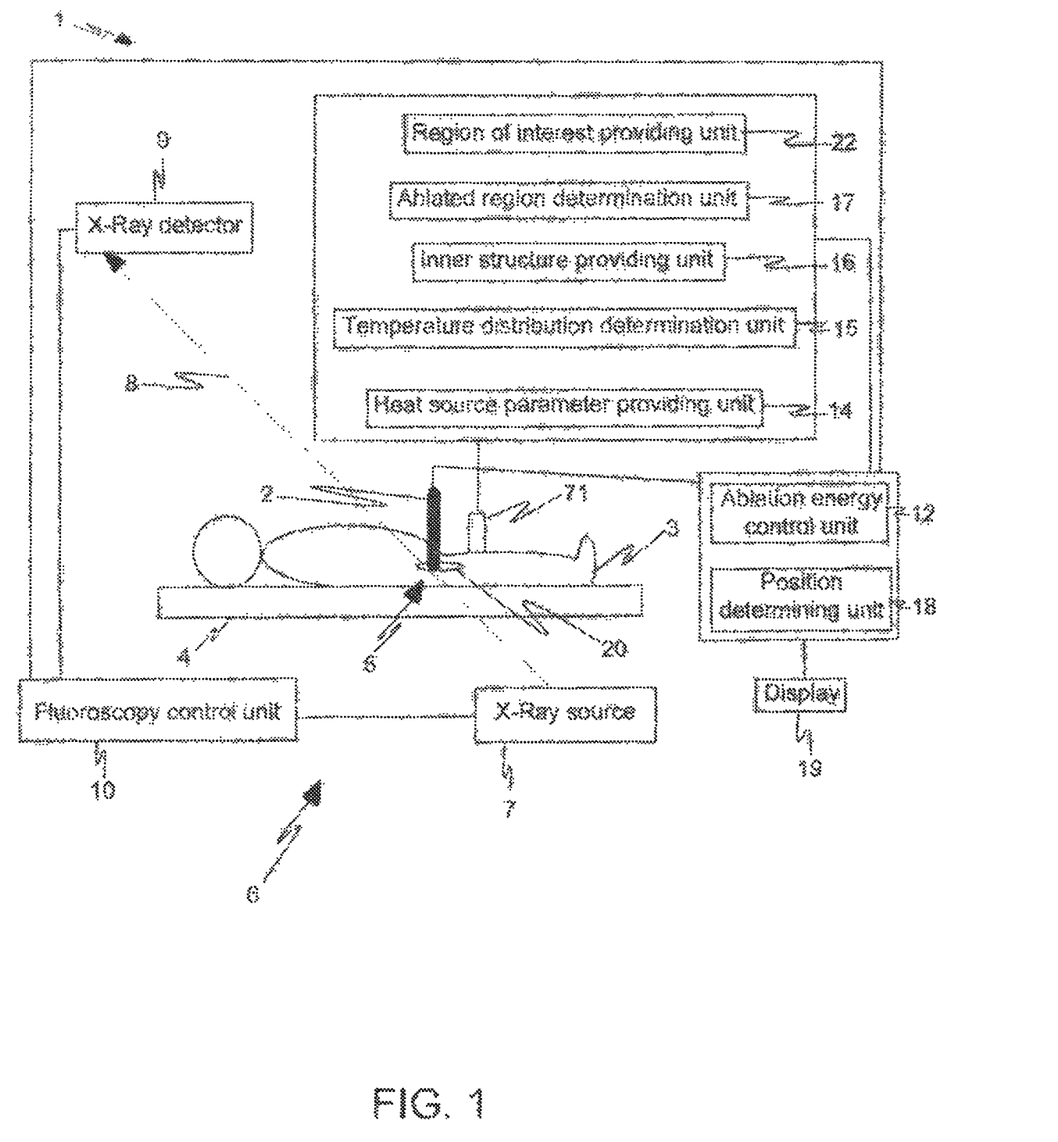
FIG. 1 shows schematically and exemplarily an embodiment of an energy application system for applying energy to a person.

FIG. 1 shows schematically and exemplarily an embodiment of an energy application system for applying energy to an object. In this embodiment the system 1 is an ablation system for ablating a tumor within a person 3 lying on a support means 4 like a patient table. The system 1 comprises an energy application element 2 for applying energy to the person 3, in particular, to a tumor within the person 3. In this embodiment the energy application element 2 is an ablation needle comprising an ablation electrode 40 and an ultrasound sensor 41 at the tip 5 of the ablation needle 2 as schematically and exemplarily illustrated in FIG. 2.

The energy applied to the person 3 by the ablation electrode 40 is preferentially RF energy, wherein the ablation electrode 40 is electrically connected to an ablation energy control unit 12, which is adapted to control the application of the RF energy. In this embodiment the ablation energy control unit 12 comprises an RF source for providing the RF energy.

The system 1 further comprises a temperature distribution determination apparatus for determining a spatially and temporally dependent temperature distribution within the person 3, while the RF energy is applied to the person 3. The temperature distribution determination apparatus comprises an ultrasound probe 71 for sending ultrasound waves 72 into an ultrasound measurement region within, in this embodiment, the liver 20 of the person 3, receiving ultrasound waves from the ultrasound measurement region and generating a time-dependent first ultrasound signal based on the received ultrasound waves.

Figure 2:
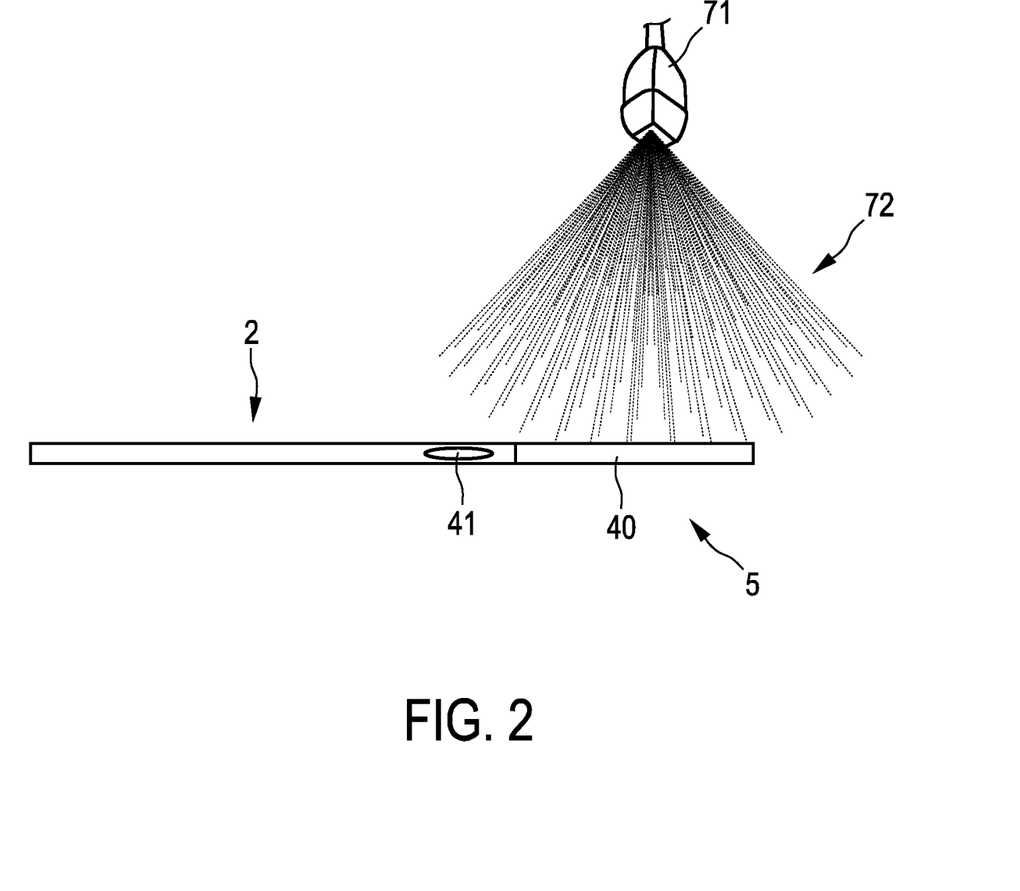
FIG. 2 shows schematically and exemplarily an embodiment of an energy application element of the energy application system.

The ultrasound sensor 41 attached to the energy application element 2 is adapted to receive the ultrasound waves 72 from the ultrasound probe 71 and to generate a second ultrasound signal based on the received ultrasound waves, wherein a position determination unit 18 is adapted to determine the position of the energy application element 2 relative to the ultrasound measurement region based on the received second ultrasound signal. The ultrasound sensor 41 and the position determination unit 18 therefore track the position of the ultrasound sensor 41 and thus of the energy application element 2 relative to the ultrasound measurement region and can be regarded as forming a tracking device for tracking the position of the energy application element 2 within the liver 20 relative to the ultrasound measurement region. The position determination unit 18 can be adapted to determine the position by using known techniques like the techniques described in US 2013/0041252 A1 or in the article "A Non-disruptive Technology for Robust 3D Tool Tracking for Ultrasound-Guided Interventions" by Jay Mung, Francois Vignon and Ameet Jain, MICCAI 1, volume 6891 of Lecture Notes in Computer Science, pages 153 to 160, Springer (2011), which are herewith incorporated by reference.

The ultrasound sensor 41 can comprise copolymer piezoelectric material for generating the second ultrasound signal based on the received ultrasound waves 72. The ultrasound sensor 41 is preferably in a passive mode only, i.e. preferentially it just receives ultrasound waves and generates an ultrasound signal based on the received ultrasound waves. Although in FIG. 2 only one ultrasound sensor is shown, in other embodiments also two or more ultrasound sensors can be attached to the energy application element.

The ultrasound measurement region can be two-dimensional or three-dimensional. If the ultrasound measurement region is two-dimensional it can be regarded as being a scan plane that is ultrasonically scanned. In an embodiment the ultrasound measurement region comprises several scan planes, which may be parallel or orthogonal to each other.

The temperature distribution determination apparatus further comprises a temperature distribution determination unit 15 for determining a temperature distribution within the liver 20 based on the generated time-dependent first ultrasound signal and based on the tracked position of the energy application element 2. In particular, the temperature distribution determination unit 15 is adapted to, in a lower temperature range, a) determine a time-dependent first temperature distribution in the ultrasound measurement region based on the generated time-dependent first ultrasound signal, b) provide a model describing a time-dependent model temperature distribution within the liver 20 depending on modifiable model parameters and depending on the position of the energy application element tracked over time, and c) determine model parameters based on the tracked position of the energy application element 2 and based on the provided model by modifying the model parameters such that the model temperature distribution is adapted to the first temperature distribution in the ultrasound measurement region, in particular, such that a deviation of the model temperature distribution from the first temperature distribution in the ultrasound measurement region is minimized. Moreover, the temperature distribution determination unit 15 is preferentially further adapted to, in a higher temperature range, determine a time-dependent second temperature distribution within the liver 20 based on the provided model and the determined model parameters. The lower temperature range is a temperature range, in which temperatures are measurable by ultrasound thermometry, whereas the higher temperature range is a temperature range, in which temperatures are not measurable by ultrasound thermometry. The modifiable parameters include object parameters like thermal parameters or electrical parameters of the object. In this embodiment a tumor in the liver 20 of the person 3 should be ablated such that the modifiable model parameters include the thermal conductivity and the electrical conductivity of the liver 20.

The model preferably further depends on heat source parameters defining the heating of the liver 20, while the energy is applied by the energy application element 2. The heat source parameters include, for instance, the times at which energy is applied to the person 3, the amount of energy applied to the person 3, et cetera. The heat source parameters can be provided by a heat source parameter providing unit 14, which may have received information about the times, at which the energy is applied, and about the amount of the applied energy from the ablation energy control unit 12. In particular, there can be a continuous data stream from the ablation energy control unit 12 to the heat source parameter providing unit 14, in order to send this information from the ablation control unit 12 to the heat source parameter providing unit 14.

The energy application element may further comprises one or several temperature sensing elements, especially thermocouples, for measuring the temperature at the tip of the energy application element 2, wherein the temperature distribution determination unit 15 may be adapted determine the model parameters such that a deviation of a) the modeled temperature distribution in the ultrasound measurement region and at the location of the energy application element 2 and b) the first temperature distribution in the ultrasound measurement region and the temperature at the location of the energy application element 2 measured by the one or several temperature sensing elements of the energy application element 2 is minimized.

In a first heating period the energy application element may heat the liver 20 to temperatures within the lower temperature range in which the first temperature distribution can be determined by ultrasound thermometry. Thus, the lower temperature range preferentially includes temperatures being smaller than 50 degrees Celsius. The first temperature distribution is determined by operating the ultrasound probe 71 to send ultrasound waves into the person 3, detecting backscattered ultrasound waves and generating a temporally dependent first ultrasound signal based on the detected backscattered ultrasound waves. The ultrasound probe 71 is a two-dimensional or three-dimensional ultrasound probe and the time-dependent first ultrasound signal is a sequence of ultrasound frames, which may also be regarded as being ultrasound images, wherein each ultrasound frame is assigned to an acquisition time.

The liver 20 and thus the energy application element 2, which has been introduced into the liver 20, periodically move due to respiration. The temperature distribution determination unit 15 is preferentially adapted to determine a motion phase of the motion of the liver 20 based on the position of the energy application element 2 tracked over time and to use for the determination of the time-dependent first temperature distribution the time-dependent first ultrasound signal, i.e. the ultrasound frames in this embodiment, at times that correspond to the determined motion phase. The determined motion phase is preferentially a quiescent phase of the motion such that preferentially only ultrasound frames are used for the determination of the first temperature distribution by ultrasound thermometry, which have been acquired in the quiescent phase. This can lead to an improved quality of the determination of the first temperature distribution.

The selection of ultrasound frames, which should be used for determining the first temperature distribution by ultrasound thermometry, can also be performed in another way based on the tracked position of the energy application element 2. For instance, the temperature distribution determination unit 15 can be adapted to use for the determination of the first temperature distribution only ultrasound frames which have been acquired, while the energy application element 2 was located at the same position relative to the ultrasound measurement region. Also this can lead to an improved quality of the determination of the first temperature distribution, because it is more likely that the selected ultrasound frames correspond to the same part of the liver 20, although the liver 20 moves due to respiration.

The temperature distribution determination unit 15 may also be adapted to use directly the acquired ultrasound frames for determining a quiescent motion phase. For example, a similarity measure can be applied to temporally adjacent ultrasound frames, wherein, if the application of the similarity measure reveals that two or more adjacent ultrasound frames are similar, it can be assumed that these ultrasound frames have been acquired, while the liver 20 was in a quiescent motion phase, wherein the ultrasound frames acquired during the quiescent motion phase in different motion periods can be used for determining the first temperature distribution by ultrasound thermometry.

The temperature distribution determination apparatus further comprises an inner structure providing unit 16 for providing inner structural data being indicative of the inner structure of the person 3, which may influence the temperature distribution, wherein the temperature distribution determination unit 15 is adapted to also consider the provided inner structural data while determining the temperature distribution, in particular, while determining the model parameters and the second temperature distribution. The inner structural data are preferentially morphological image data like computed tomography (CT) or magnetic resonance image (MRI) data, which show the inner structure of the person 3.

In an embodiment in the first heating period, in which the energy application element 2 heats the liver tissue to a temperature within the lower temperature range in which a temperature distribution is measurable by ultrasound thermometry, the ultrasound probe 71 sends ultrasound waves to the liver tissue, detects backscattered ultrasound waves and generates a time-dependent first ultrasound signal, i.e. in this embodiment ultrasound frames for different times. The temperature distribution determination unit 15 then determines the time-dependent first temperature distribution based on the generated time-dependent first ultrasound signal, wherein not all ultrasound frames are used for determining the time-dependent first temperature distribution by ultrasound thermometry, but only ultrasound frames corresponding to a quiescent motion phase and/or to a same position of the energy application element 2 relative to the ultrasound measurement region. After that, the temperature distribution determination unit 15 determines model parameters of the thermal model like thermal and electrical conductivities of the liver tissue by adapting the model such that a deviation between a modeled temperature distribution defined by the model and the first temperature distribution is minimized. During the modeling the position, especially the distance, of the energy application element 2, i.e. of the heating source, relative to the ultrasound measurement region, the inner structural data and heat source parameters like the amount of heat generated by the energy application element 2 and the heating times are considered. In particular, for modeling the temperature distribution the thermal model may be initialized by using the inner structural data, which in this embodiment is preferentially a medical image of the liver 20 including the tumor region like an CT or MR image, wherein the tumor and other structures like blood vessels are identified and segmented in the medical images and this information is used together with initial model parameter values for providing an initialized thermal model. For instance, thermal and electrical parameters of the different identified and segmented structures can be initially provided for providing an initial thermal model. The initial model parameters can be tissue properties like the thermal conductivity and the electrical conductivity of different kinds of tissue or other parameters like perfusion parameters, directional flow parameters, et cetera. Perfusion parameters and directional flow parameters may be initially determined by using already known information, which may be known from other measurements, which may have been performed before. For instance, an ultrasound Doppler measurement can be performed, in order to determine typical flow velocities and perfusion parameters. In an embodiment the initial model has already been determined and initialized in advance and just needs to be loaded from a storing unit of the temperature distribution determination unit 15.

The thermal model is preferentially a finite element implementation of the Bio-Heat Transfer Equation (BHTE) proposed by H. H. Pennes, for example, in the article "Analysis of tissue and arterial blood temperatures in the resting human forearm", 85:5-34, Journal of Applied Physiology (1998), which is herewith incorporated by reference.

The BHTE models thermal diffusion and perfusion. It includes a modeling of the heat source, i.e. of the energy application element 2, wherein a Laplace equation is implemented. The model preferentially considers directional flow in large blood vessels by using equations for heat transfer in fluids. In the case of a model for liver tissue initial model parameters are, for instance, an electrical conductivity of 0.148 S/m, a thermal conductivity of 0.465 W/mC, a density of 1060 kg/m$^3$, a heat capacity of 3600 J/Ckg and a perfusion rate of $6.4 \times 10^{-3}$/s. Further initial model parameters can be properties of the energy application element 2 as documented by the respective manufacturer, in order to consider an influence of the energy application element properties on the electrical current distribution and the heat transfer.

After the model parameters have been determined by minimizing the deviation between the first temperature distribution and the modeled temperature distribution, in a second heating period, in which the liver tissue is heated to ablative temperatures above 50 degrees Celsius, i.e. to the higher temperature range in which temperatures are not measurable by ultrasound thermometry, the temperature distribution determination unit 15 models the second temperature distribution by using the thermal model with the model parameters, i.e. in this case the tissue parameters like the thermal and electrical conductivities, which have been determined in the first heating period. The modeling of the second temperature distribution preferentially also considers the heat source parameters like the amount of heat generated by the energy application element 2 and the heating times and the tracked position of the energy application element 2. Moreover, the temperature distribution determination unit 15 can be adapted to also consider temperatures measured by one or several temperature sensing elements like thermocouples, which may be attached to the energy application element 2. For instance, the temperature distribution determination unit 15 can be adapted to model the second temperature distribution based on the thermal model with the determined model parameters such that at the location of the energy application element 2 the temperature of the modeled second temperature distribution is similar to the temperature measured by the temperature sensing elements.

The temperature distribution determination apparatus further comprises an ablated region determination unit 17 for determining an ablated region defining a region within the liver 20 that has been ablated, wherein the ablated region determination unit 17 is adapted to determine the ablated region by determining a part of the liver 20 for which the modeled second temperature distribution comprises a temperature being larger than a predefined temperature threshold. The temperature distribution determination apparatus also comprises a region of interest providing unit 22 for providing a region of interest being, in this embodiment, the tumor region, which should be ablated, wherein the determined ablated region and the tumor region can be shown on a display 19. For instance, an overlay of the determined ablated region and the tumor region can be shown on the display 19. The predefined temperature threshold is, for instance, 60, 65 or 70 degrees Celsius.

The ablation energy control unit 12 can be adapted to control the energy application element 2, i.e. the power of ablation, depending on the determined second temperature distribution. In particular, the ablation energy control unit 12 can be adapted to control the ablation power such that the tumor region is completely ablated.

For navigating the energy application element 2 to the liver 20 ultrasound images generated by the ultrasound probe 71 may be used. Alternatively or in addition, an x-ray fluoroscopy system 6 for generating fluoroscopy images showing the energy application element 2 within the person 3 may be used for navigating the energy application element 2 to the liver 20. The x-ray fluoroscopy system 6 is preferentially an x-ray C-arm system comprising an x-ray source 7 for generating x-rays 8 which traverse the person 3 on the table 4 and an x-ray detector 9 for detecting the x-rays 8 after having traversed the person 3. The x-ray fluoroscopy system 6 further comprises a fluoroscopy control unit 10 for controlling the x-ray source 7 and the x-ray detector 9. The x-ray detector 9 generates x-ray images of the person 3, which can be shown on the display 19. The x-ray fluoroscopy system 6 can also be used to acquire x-ray images from different acquisition directions, wherein the fluoroscopy control unit 10 may be adapted to reconstruct a computed tomography image based on these x-ray images acquired in different acquisition directions. The reconstructed computed tomography image shows the inner structure of the person 3 and can be used when modeling a temperature distribution as inner structural data.

In this embodiment the energy application element 2 is navigated directly by hand. In another embodiment the system can further comprise a navigation unit for navigating the energy application element, in particular, the ablation needle, to a desired location within the person. The navigation unit can be adapted to allow a user to navigate the energy application element completely by hand or semi-automatically. The energy application element may comprise built-in guiding means, which can be controlled by the navigation unit. The energy application element can, for example, be steered and navigated by the use of steering wires, in order to guide the energy application element to a desired location within the person.

Figure 3:
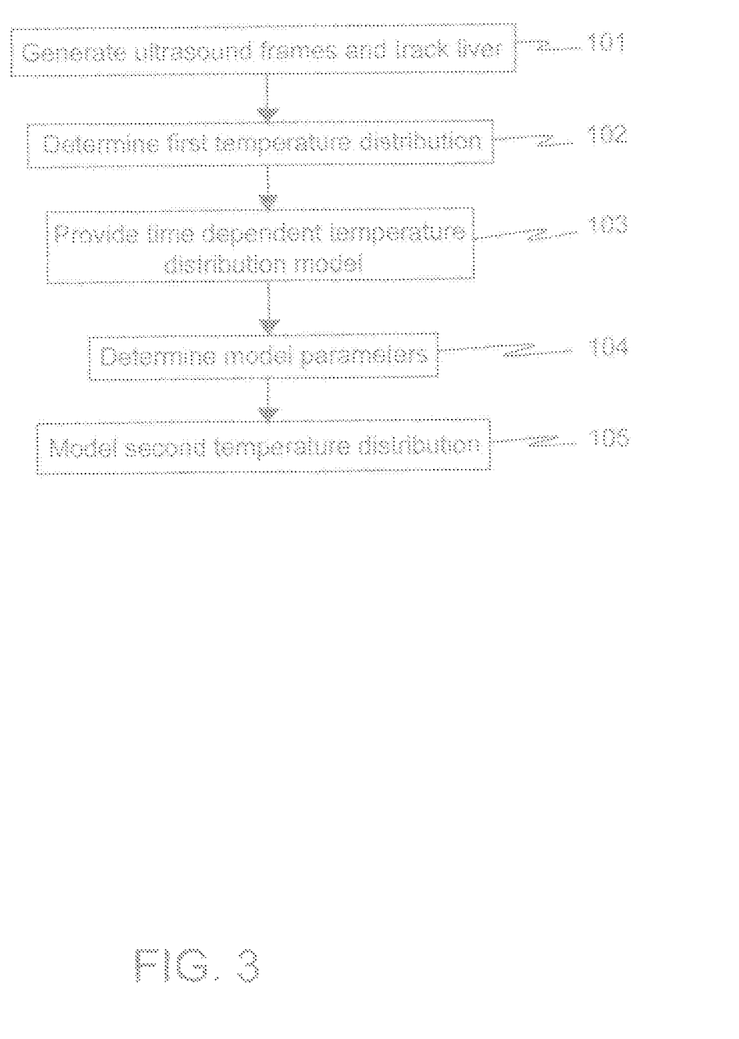
FIG. 3 shows a flowchart exemplarily illustrating an embodiment of a temperature distribution determination method for determining a temperature distribution within the person, while the energy application element applies energy to the person and thereby heats the person.

In the following an embodiment of a temperature distribution method will exemplarily be described with reference to a flowchart shown in FIG. 3.

In step 101 ultrasound waves are sent into the ultrasound measurement region within the liver 20, ultrasound waves are received from the ultrasound measurement region and a time-dependent first ultrasound signal, i.e. in this embodiment ultrasound frames for different times, is generated based on the received ultrasound waves by the ultrasound probe 71. Moreover, in step 101 the position of the energy application element within the liver is tracked by the tracking device. Step 101 is performed in a first heating period, in which the liver 20 is heated by the energy application element 2 to a temperature within the lower temperature range in which a temperature is measureable by ultrasound thermometry.

In the following steps the time-dependent first ultrasound signal and the tracked position of the energy application element are used for determining a temperature distribution, especially a first temperature distribution and a second temperature distribution. In step 102 ultrasound frames, which have been acquired during a quiescent motion phase of the liver and/or while the energy application element was at the same distance relative to the ultrasound measurement region, are selected and used to determine the first temperature distribution by ultrasound thermometry. In step 103 a model is provided, which describes a time-dependent model temperature distribution within the liver 20 depending on modifiable model parameters like electrical and thermal conductivities of liver tissue and depending on the position of the energy application element over time. In step 104 the model parameters are determined based on the tracked position of the energy application element and based on the provided model by modifying the model parameters such that a deviation of the model temperature distribution from the determined first temperature distribution in the ultrasound measurement region is minimized. In step 105, which is performed while the energy application element heats the liver tissue to a temperature within the higher temperature range in which a temperature is not measurable by ultrasound thermometry and in which liver tissue can be ablated, the temperature distribution determination unit 15 models the second temperature distribution based on the provided thermal model and the determined model parameters.

Thermal ablation techniques are excellent alternatives to major surgery, which can pose a risk even with the most experienced surgeon. These techniques are minimally invasive requiring only needles, which may be adapted to perform an RF therapy, a cryotherapy or a microwave ablation therapy, or they are non-invasive, wherein, for instance, a non-invasive heat source such as an ultrasound heating source like a high intensity focused ultrasound (HIFU) source is used. In most of the procedures, cancerous tissue is heated to temperatures above 60 degrees Celsius and coagulated.

For performing an RF ablation (RFA) procedure the system described above with reference to FIG. 1 comprises a probe with an active electrode tip, i.e. the energy application element 2, through which preferentially a 460 to 500 kHz alternating current is conducted. The current propagates through the body of the person 3 to grounding pads (not shown in FIG. 1 for clarity reasons) placed either on the back or the thigh of the person 3. The current causes ionic agitation and frictional heating. Heat is then dissipated through thermal conduction to ablate the tumor region. In this embodiment RFA is used to treat liver cancer.

In the embodiment described above with reference to FIG. 1 RFA is performed under x-ray guidance by using an x-ray C-arm system and/or by ultrasound guidance by using the ultrasound probe. However, the RFA can also be performed by using another guidance system, which may be based on CT imaging or MR imaging. A follow-up examination is preferentially done by using a CT scan or MRI scan within, for example, a month to assess effectiveness of ablation and again at three months intervals along with tumor markers to detect residual disease or recurrence. After state of the art ablation procedures have been performed, relatively high recurrence rates are often observed because of the often present inability to monitor and control ablation size sufficiently to adequately kill the tumor cells. The system described above with reference to FIG. 1 provides therefore preferentially realtime feedback to the clinician by providing a temperature map of the ablated zone. This could also be achieved with reasonable accuracy with MR based temperature imaging. However, MR imaging is expensive and may not be readily available. Ultrasound is another modality that may be used for image guidance during placement of the needle. Due to its ease of use and availability it may be a preferred method for monitoring the lesions. However, in the prior art ultrasound is used generally for monitoring the treatment by visualizing the hyperechoic lesions on a B-mode image. Such visualization is only approximate and not a good indicator of the treatment efficacy.

The system described above with reference to FIG. 1 uses an ultrasound probe and a temperature distribution determination unit for determining a first temperature distribution by two-dimensional or three-dimensional ultrasound thermometry. The underlying principle of ultrasound thermometry is that the speed of sound in tissue changes as a function of temperature which manifests as apparent shifts, i.e. displacements, in ultrasound echoes. The resulting "temperature-induced strain", which is mathematically derived by differentiating the displacement along the ultrasound beam direction, is nominally proportional to the temperature rise in the range up to 50 degrees Celsius. However, the problem lies in the variation in trend of the temperature dependence of speed of sound for various tissues. For example, for liver tissues the speed of sound increases approximately linearly with temperature up to a temperature range of 50 degrees Celsius, after which the trend plateaus. Hence, there is no sensitivity to ultrasound echo shifts with temperatures beyond this temperature range. Also, with the onset of tissue necrosis and the resulting changes in tissue structure, the signature of the ultrasound echoes changes significantly and makes the comparison of ultrasound echoes to determine the displacement difficult. Therefore, for temperatures above 50 degrees Celsius the ultrasound thermometry, which is based on tracking changes in speed of sound, is not a reliable indicator of temperature in the tissue.

A critical input into the thermal model is the spatial location where the measurement was made, i.e. the location of the ultrasound measurement region, with respect to the location of the energy application element, in particular, with respect to the location of an ablation electrode. When the thermal gradients are relatively large, an uncertainty in the position of the ultrasound measurement region, which may be a scan plane, relative to the position of the energy application element can result in large errors in the determined model parameters. In addition, physiological motion like respiratory motion can amplify the problem of not being able to determine the position of the ultrasound measurement region relative to the energy application element accurately and can introduce errors in the ultrasound thermometry estimates, i.e. in the first temperature distribution determined by ultrasound thermometry. Since ultrasound thermometry relies on the ability to track phase changes in ultrasound echoes acquired at different time instants, the accuracy of the ultrasound thermometry depends on whether an ultrasound signal at different time instants, which are compared for determining a temperature by ultrasound thermometry, originates from the same tissue region. The temperature distribution determination apparatus can be adapted such that only ultrasound acquisitions are used for determining a temperature by ultrasound thermometry, which correspond to the same position of the energy application element, in particular, of the ablation electrode, and to a same position of the ultrasound measurement region relative to the position of the energy application element, which of course corresponds to the same position of the energy application element relative to the position of the ultrasound measurement region. For determining the position of the energy application element relative to the ultrasound measurement region the temperature distribution determination unit preferentially uses an ultrasound sensor based tracking technology as disclosed, for instance, in US 2013/0041252 A1 or in the above mentioned article by Jay Mung et al. The ultrasound sensor based tracking is preferentially adapted such that it provides a three-dimensional positional accuracy with errors being smaller than 1 mm. The tracking information from the ultrasound sensor can be used to get the location of the energy application element, in particular, of the ablation electrode, wherein this tracking information can be used to track changes in the location of the energy application element, which in turn can be used to obtain information about respiratory motion. Based on the obtained information about respiratory motion the ultrasound acquisition can be gated during the quiescent phase of the motion. The tracking information obtained by using the ultrasound sensor may further be used to determine the distance of the ultrasound measurement region from the energy application element, i.e. the position of the energy application element relative to the position of the ultrasound measurement region.

The temperature distribution determination unit is preferentially adapted to solve inaccuracies in determining temperature distributions caused by physiological motions and caused by incorrect thermometry data in the thermal model. In particular, motion caused by respiration can lead to erroneous estimates of temperatures determined by using ultrasound. Motion can confound the echo-tracking algorithm used in ultrasound thermometry by causing exaggerated additional echo shifts and in some cases de-correlation of the echoes. Regarding the aspect of incorrect thermometry data in the thermal model, it is noted that the accuracy of the modeled temperature depends on the accuracy of the position of the ultrasound measurement region with respect to the position of the energy application element. The temperature distribution determination unit is therefore preferentially adapted to use the position of the ultrasound measurement region relative to the position of the energy application element, in particular, the distance between the ultrasound measurement region and an ablation electrode, when modeling a temperature distribution.

The positional information obtained by using the one or several ultrasound sensors may be regarded as representing local respiration induced motion. By using this information, ultrasound data can be acquired at the resting phase of the respiration cycle. Moreover, the positional information obtained by using the one or several ultrasound sensors defines the position, especially the distance, of the ultrasound measurement region to the ablation electrode, wherein this information can be coupled to the thermal model that estimates the temperature distribution.

The system described above with reference to FIG. 1 can be adapted to continuously track the position of the energy application element, in particular, of an ablation electrode and/or an introducer, and to record the position in the ultrasound coordinate system defined by the ultrasound probe. Based on the continuously tracked position of the energy application element a motion waveform may be determined and this motion waveform may be used to detect quiescent phases of the motion. This knowledge about the quiescent motion phases can then be used to select ultrasound acquisitions, which correspond to these quiescent motion phases. However, the acquisition of the ultrasound data, i.e. of the first ultrasound signal, can also be controlled such that ultrasound data are acquired only in quiescent motion phases determined from the continuously tracked position of the energy application element. The continuously tracked position of the energy application element is preferentially also used by the thermal model such that the ultrasound thermometry data, i.e. in the embodiment described above with reference to FIG. 1 the first temperature distribution, is considered in the thermal model at the correct position of the ultrasound measurement region with respect to the position of the energy application element.

The system described above with reference to FIG. 1 is preferentially adapted to combine ultrasound thermometry and thermal modeling, in order to monitor a temperature rise during an ablation procedure, i.e. in the second heating period, and to finally estimate the dimensions of the ablated region. In a pre-treatment phase the ultrasound probe, which may be a two-dimensional or a three-dimensional ultrasound probe, can be used to identify possible insertion paths of the energy application element into the tumor within the liver. Furthermore, during the first heating period, i.e. during the low power heating phase of the treatment, the same ultrasound probe may be used to acquire ultrasound backscatter data, i.e. the first ultrasound signal, for obtaining thermometry estimates, i.e. the first temperature distribution. The system is preferably adapted to track the position of the energy application element and to obtain position coordinates of the energy application element for a) obtaining motion-gated ultrasound thermometry frames, i.e. motion-gated first temperature data, and b) accurately inputting into the thermal model to which positions the motion-gated ultrasound thermometry frames refer. If the ultrasound measurement region is a two-dimensional scan plane, the ultrasound probe is preferentially adapted such that the elevation ultrasound beam width has a coverage being sufficient to produce a signal on the ultrasound sensor attached to the energy application element, even if it is a few millimeters lateral distance away.

When the ultrasound sensor attached to the energy application element is within the field of view of the ultrasound probe, the ultrasound sensor is sensitive to the acoustic energy emitted by the ultrasound probe. When the ultrasound beams emitted by the ultrasound probe interact with the ultrasound sensor attached to the energy application element, electrical signals are generated, which can be used to continuously determine the position, especially the distance, between the ultrasound sensor and the ultrasound probe based on time-of-flight calculations. Thus, the location of the ultrasound sensor and hence the energy application element can be continuously tracked in the context of the ultrasound coordinate system.

The energy application element with the ultrasound sensor moves due to physiological motion. Since the position of the ultrasound sensor is tracked, a motion profile or motion waveform is obtained. Ultrasound thermometry estimates temperature based on the analysis of ultrasound backscatter obtained at two instants of time. For accurate temperature estimates using ultrasound thermometry, the frame to frame change in ultrasound backscatter should not be corrupted by any external motion. Therefore, the system described above with reference to FIG. 1 is preferentially adapted to minimize the effect of motion by using ultrasound data at quiescent motion phases only. The motion profile or motion waveform may be used to identify time instants at which the energy application element and hence the liver as a whole is in the quiescent motion phase. At those identified instants of time the ultrasound data are preferentially used for thermometry calculations. Additionally, if the energy application element does not come back to its original position, other motion compensation mechanisms may be employed to remove any residual mechanical motion. For instance, ultrasound frames may be registered to each other by using image-based speckle tracking, wherein the registered frames may be used for determining a temperature distribution, in particular, the first temperature distribution, by ultrasound thermometry.

The continuous tracking of the energy application element within the coordinate system of the ultrasound probe, which may be determined based on pulse-echo analysis and based on the knowledge about the geometry of the ultrasound probe, allows the tracking device to determine the position of the energy application element relative to the ultrasound measurement region. In particular, if the ultrasound measurement region is formed by one or several two-dimensional scan planes, the distance of the energy application element to these one or several scan planes can be determined. The position of the ultrasound measurement region, in particular, of the one or several scan planes, relative to the energy application element can be input into the thermal model, while determining the model parameters, especially tissue parameters like electrical and thermal conductivities. This information is preferably also used when modeling the temperature distribution during the ablation procedure, i.e. in the second heating period, when the thermal model is used together with the determined model parameters for determining the temperature distribution during the ablation procedure. If the position of the ultrasound measurement region relative to the energy application element changes, these changes can be considered in the thermal model while determining the model parameters in the first heating period and while determining the second temperature distribution in the second heating period.

Further tracking techniques can be additionally used for tracking the position of the energy application element relative to the ultrasound measurement region. For instance, EM or OSS based techniques can be additionally used to obtain the position of the energy application element relative to the ultrasound measurement region and to track the motion. For instance, especially if the ultrasound probe is a two-dimensional ultrasound probe, EM sensors can be placed on the energy application element, the ultrasound probe and a reference point, in order to determine the position of the energy application element and the position of the ultrasound probe relative to the reference point and, thus, the position of the energy application element relative to the ultrasound measurement region, which is defined by the configuration of the ultrasound probe and the determined position of the ultrasound probe. If in addition to the position, which has been determined based on the second ultrasound signal generated by the ultrasound sensor attached to the energy application element, a further position is determined based on an additional tracking technique like an EM or OSS based tracking technique, these positions may be combined to a final position to be used by the temperature distribution determination unit for determining the temperature distribution. For instance, these positions can be weightedly averaged, wherein the weights may be determined by calibration.

Although in above described embodiments only the tracked position of the energy application element is used for estimating the motion of the liver caused by respiration, in another embodiment additional tissue motion may be observed in ultrasound frames generated by the ultrasound probe and this additional tissue motion may be used in combination with the motion, which has been determined based on the tracked position of the energy application element, for determining certain motion phases, in particular, for determining a quiescent motion phases. This can lead to an improved estimation of the tissue motion. For example, if based on the tracked motion of the energy application element and thus of the liver certain ultrasound frames are regarded as being ultrasound frames having been acquired in quiescent motion phases, from these ultrasound frames a subgroup of registered ultrasound frames can be selected, wherein it can be determined which ultrasound frames are registered to each other based on image-based speckle tracking. The selected ultrasound frames can then be used for determining a temperature distribution, in particular, a first temperature distribution, by ultrasound thermometry.

The temperature distribution determination unit can also be adapted to determine a relative motion additionally established between consecutive ultrasound frames by analyzing the difference in the ultrasound sensor signal and/or the ultrasound frames from one ultrasound frame to the next. This information can provide an estimate of the "derivative" of the motion signal and can be used for improved motion estimation. In particular, to estimate the relative motion of the energy application element with respect to the tissue, two motions can be computed between any two consecutive ultrasound frames. Firstly, a tissue motion map may be estimated for a whole ultrasound image using well-known motion map creation methods like optical flow or sum-squared-difference (SSD) techniques. The tissue motion maps define in what way the tissue has moved between the frames. In addition, the second ultrasound signal generated by the ultrasound sensor attached to the energy application element can be used to provide the absolute position of the energy application element in each ultrasound frame. Putting these data together, the relative motion between the energy application element and the tissue can be determined and displayed on the display 19. These data can additionally be used as an input into the ultrasound thermometry determination and also into the thermal model, in order to further improve the accuracy of determining the temperature distributions.

Although in above described embodiments only a single energy application element has been introduced into the person, in other embodiments several energy application elements, in particular, several ablation needles, may be inserted into the person, especially into the tissue, in order to estimate motion at different points. If several energy application elements, each equipped with at least one ultrasound sensor, are used, the three-dimensional position of the ultrasound probe relative to the energy application elements may be determined. Thus, the three-dimensional position of the ultrasound probe may be tracked and this tracked position may be used to reconstruct a three-dimensional temperature map as the ultrasound probe is moved around the region of interest. Although this can be achieved by even one energy application element with an asymmetric distribution of ultrasound sensors, using two or more energy application elements, wherein each energy application element is equipped with at least one ultrasound sensor, can provide an increased robustness. This can also be useful as all the ultrasound frames can now be utilized to create a "thick slice" thermometry map even without moving the ultrasound probe due to the natural motion of the tissue.

Although in above described embodiments a model is used for determining a temperature distribution, in another embodiment the temperature distribution determination unit may just be adapted to determine a temperature by ultrasound thermometry, wherein for the determination of the temperature distribution by ultrasound thermometry only ultrasound frames are used, which have been selected based on, for instance, the tracked position of the energy application element relative to the ultrasound measurement region. For instance, the tracked position of the energy application element relative to the ultrasound measurement region can be used to identify certain motion phases, wherein only ultrasound frames may be used, which have been acquired in these motion phases. Alternatively or in addition, only ultrasound frames may be used for determining the temperature distribution, which have been acquired while the energy application element was at a same position relative to the ultrasound measurement region.

Although in above described embodiments the temperature distributions are determined in the liver, in other embodiments the temperature distributions can be determined in another part of a living being like another organ. Moreover although in above described embodiments the energy application element is an ablation element comprising a single ablation electrode, in other embodiments the energy application element can be configured in another way. For instance, it can be an ablation element comprising several ablation electrodes. Moreover, the ablation element may comprise one or several temperature sensing elements like one or several thermocouples. Furthermore, the ablation element may not be an RF ablation element, but it may be an ablation element for ablating tissue in another way. For instance, it may be an HIFU ablation element, a microwave ablation element, a laser ablation element, et cetera.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of a temperature distribution by ultrasound thermometry, the determination of model parameters, the determination of a model temperature, et cetera performed by one or several units or devices can be performed by any other number of units or devices. These procedures and/or the control of the temperature distribution determination apparatus in accordance with the temperature distribution determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a temperature distribution determination apparatus for determining a temperature distribution within an object, while an energy application element applies energy to the object, especially while an ablation procedure for ablating a tumor within an organ is performed. A time-dependent first ultrasound signal is generated for an ultrasound measurement region within the object and a temperature distribution within the object is determined based on the generated time-dependent first ultrasound signal and based on a position of the energy application element relative to the ultrasound measurement region tracked over time. This can ensure that always the correct position of the energy application element, which may be regarded as being a heat source, is considered, even if the energy application element moves, for instance, due to a movement of the object. This can lead to a more accurate determination of the temperature distribution.

The invention claimed is:

1. A temperature distribution determination apparatus for determining a temperature distribution within an object, while an energy application element applies energy to the object, the temperature distribution determination apparatus comprising:
a single ultrasound device configured to send ultrasound waves into an ultrasound measurement region within the object, to receive ultrasound waves from the ultrasound measurement region and to generate a time-dependent first signal based on the received ultrasound waves,
an ultrasound sensor attached to the energy application element and configured to receive the ultrasound waves sent by the single ultrasound device and to generate a second signal based on the received ultrasound waves, and
a computer processor configured to:
track a position of the energy application element relative to the ultrasound measurement region tracked over time based on the second signal, and
determine a temperature distribution within the object based on the generated time-dependent first signal and based on the position of the energy application element relative to the ultrasound measurement region tracked over time.

2. The temperature distribution determination apparatus as defined in claim 1, wherein the computer processor is further configured to:
in a lower temperature range,
determine a time-dependent first temperature distribution in the ultrasound measurement region based on the generated time-dependent first signal,
provide a model describing a time-dependent model temperature distribution within the object depending on modifiable model parameters and depending on the position of the energy application element tracked over time,
determine model parameters based on the tracked position of the energy application element and based on the provided model by modifying the model parameters such that the model temperature distribution is adapted to the first temperature distribution in the ultrasound measurement region, and
in a higher temperature range:
determine a second temperature distribution within the object based on the provided model and the determined model parameters.

3. The temperature distribution determination apparatus as defined in claim 2, wherein the computer processor is further configured to:
determine the time-dependent first temperature distribution based on the generated time-dependent first signal and based on the position of the energy application element tracked over time.

4. The temperature distribution determination apparatus as defined in claim 1, wherein the object undergoes periodic motion, the periodic motion including a quiescent phase, and the energy application element is configured to be in contact with the object, in order to apply the energy to the object, and move with the object,
wherein the temperature distribution is determined at times that correspond to the quiescent motion phase.

5. The temperature distribution determination apparatus as defined in claim 1, wherein the object is a periodically moving object and the energy application element is configured to be in contact with the object, in order to apply the energy to the object, and move with the object, wherein the temperature distribution is determined at times at which the energy application element is in a common position of the energy application element in each cycle of the periodic movement.

6. The temperature distribution determination apparatus as defined in claim 1, wherein the object is a periodically moving object and the energy application element is configured to be in contact with the object, in order to apply the energy to the object, and move with the object, wherein the computer processor is further configured to:
determine a motion phase of the motion of the object based on the position of the energy application element tracked over time, and
use for the determination of the temperature distribution the time-dependent first signal at times that correspond to the determined motion phase.

7. The temperature distribution determination apparatus as defined in claim 1, wherein the object is a periodically moving object and the energy application element is in configured to be in contact with the object, in order to apply the energy to the object, and move with the object, wherein the computer processor is further configured to:

use for the determination of the temperature distribution the time-dependent first signal at times at which the tracking device determined a same position for the energy application element.

8. The temperature distribution determination apparatus as defined in claim 1, wherein the object is a part of a living being and the energy is applied to the living being for ablating the object, wherein the computer processor is further configured to:

determine an ablated region defining a region within the object that has been ablated by determining a part of the object for which the determined temperature distribution comprises a temperature being larger than a predefined temperature threshold.

9. An energy application system for applying energy to an object, the energy application system comprising:

an energy application element for applying the energy to the object, and a temperature distribution determination apparatus for determining a temperature distribution within the object caused by applying the energy to the object as defined in claim 1.

10. A temperature distribution determination method for determining a temperature distribution within an object, while an energy application element applies energy to the object, the temperature distribution determination method comprising:

sending ultrasound waves into an ultrasound measurement region within the object, receiving ultrasound waves from the ultrasound measurement region and generating a time-dependent first ultrasound signal based on the received ultrasound waves by an ultrasound device, tracking the position of the energy application element within the object relative to the ultrasound measurement region over time using an ultrasound sensor, which is attached to the energy application element, which receives the ultrasound waves from the ultrasound device and which generates a second ultrasound signal based on the received ultrasound waves, determining the position of the energy application element based on the received second ultrasound signal, and determining a temperature distribution within the object based on the generated time-dependent first ultrasound signal and based on the position of the energy application element relative to the ultrasound measurement region tracked over time.

11. The temperature distribution determination method of claim 10, wherein the step of determining the temperature distribution within the object comprises:

determining a time-dependent first temperature distribution in the ultrasound measurement region based on the generated time-dependent first ultrasound signal in a lower temperature range, providing a model describing a time-dependent model temperature distribution within the object depending on modifiable model parameters and depending on the position of the energy application element tracked over time, determining model parameters based on the tracked position of the energy application element and based on the provided model by modifying the model parameters such that the model temperature distribution is adapted to the first temperature distribution in the ultrasound measurement region, determining a second temperature distribution within the object based on the provided model and the determined model parameters in a higher temperature range.

12. The temperature distribution determination method of claim 10, wherein the temperature distribution is determined based on the position of the energy application element tracked over time.

13. The temperature distribution determination method of claim 10, wherein the object is a periodically moving object and the energy application element is configured to be in contact with the object, in order to apply the energy to the object, and move with the object, further comprising the step of:

determining a motion phase of the motion of the object based on the position of the energy application element tracked over time, and wherein:

the temperature distribution is determined at times that correspond to a quiescent motion phase.

14. The temperature distribution determination method of claim 10, wherein the object undergoes periodic movement and the energy application element is configured to be in contact with the object, to apply the energy to the object, and to move with the object, wherein the temperature distribution is determined at a common position of the energy application element in each cycle of the periodic movement.

15. The temperature distribution determination method of claim 10, wherein a movement of the object is determined based on the generated time-dependent first ultrasound signal and the temperature distribution is determined based on the generated time-dependent first ultrasound signal, the position of the energy application element tracked over time and the determined movement of the object.

16. The temperature distribution determination method of claim 10, wherein the object is a part of a living being and the energy is applied to the living being for ablating the object, an ablated region is determined defining a region within the object that has been ablated by determining a part of the object for which the determined temperature distribution comprises a temperature being larger than a predefined temperature threshold.

17. A computer program product for determining a temperature distribution within an object, the computer program product comprising program code encoded on a non-transient computer-readable medium for causing a temperature distribution determination apparatus to carry out the steps of:

sending ultrasound waves into an ultrasound measurement region within the object, receiving ultrasound waves from the ultrasound measurement region and generating a time-dependent first ultrasound signal based on the received ultrasound waves by an ultrasound device, tracking the position of the energy application element within the object relative to the ultrasound measurement region over time with an ultrasound sensor, which is attached to the energy application element, which receives the ultrasound waves from the ultrasound device, and which generates a second ultrasound signal based on the received ultrasound waves, and determines positions of the energy application element based on the received second ultrasound signal, and determining a temperature distribution within the object based on the generated time-dependent first ultrasound signal and based on the position of the energy application element relative to the ultrasound measurement region tracked over time.

* * * * *